US009688651B2

(12) United States Patent
Brundel et al.

(10) Patent No.: US 9,688,651 B2
(45) Date of Patent: Jun. 27, 2017

(54) GERANYL GERANYL ACETONE ANALOGS AND USES THEREOF

(71) Applicants: NYKEN Holding B.V., Groningen (NL); Rijksuniversiteit Groningen, Groningen (NL); Academisch Ziekenhuis Groningen, Groningen (NL)

(72) Inventors: Bianca Johanna Josephina Maria Brundel, Groningen (NL); Hermannus Steen, Groningen (NL); André Heeres, Groningen (NL); Johannes Paulus Gerardus Seerden, Groningen (NL)

(73) Assignees: Nyken Holding B.V., Groningen (NL); Rijksuniversiteit Groningen, Groningen (NL); Academisch Ziekenhuis Groningen, Groningen (NL)

( * ) Notice: Subject to any disclaimer, the term of this patent is extended or adjusted under 35 U.S.C. 154(b) by 0 days.

(21) Appl. No.: 14/394,933

(22) PCT Filed: Apr. 19, 2013

(86) PCT No.: PCT/NL2013/050295
§ 371 (c)(1),
(2) Date: Oct. 16, 2014

(87) PCT Pub. No.: WO2013/157955
PCT Pub. Date: Oct. 24, 2013

(65) Prior Publication Data
US 2015/0152076 A1 Jun. 4, 2015

Related U.S. Application Data

(63) Continuation-in-part of application No. PCT/NL2012/050262, filed on Apr. 19, 2012.

(51) Int. Cl.
| | | |
|---|---|---|
| C07D 309/12 | (2006.01) |
| C07D 261/12 | (2006.01) |
| C07D 231/20 | (2006.01) |
| C07C 311/03 | (2006.01) |
| C07C 69/738 | (2006.01) |
| C07C 49/203 | (2006.01) |
| C07D 311/46 | (2006.01) |
| C07D 231/12 | (2006.01) |
| C07D 261/08 | (2006.01) |
| C07C 235/46 | (2006.01) |
| C07C 235/88 | (2006.01) |
| C07D 207/404 | (2006.01) |
| C07C 311/09 | (2006.01) |
| C07C 311/16 | (2006.01) |
| C07C 317/44 | (2006.01) |
| C07C 233/09 | (2006.01) |
| C07C 233/56 | (2006.01) |

(Continued)

(52) U.S. Cl.
CPC .......... *C07D 309/12* (2013.01); *C07C 49/203* (2013.01); *C07C 69/738* (2013.01); *C07C 233/09* (2013.01); *C07C 233/56* (2013.01); *C07C 233/91* (2013.01); *C07C 235/46* (2013.01); *C07C 235/88* (2013.01); *C07C 237/06* (2013.01); *C07C 237/22* (2013.01); *C07C 311/03* (2013.01); *C07C 311/09* (2013.01); *C07C 311/16* (2013.01); *C07C 317/44* (2013.01); *C07D 207/404* (2013.01); *C07D 231/12* (2013.01); *C07D 231/20* (2013.01); *C07D 261/08* (2013.01); *C07D 261/12* (2013.01); *C07D 311/46* (2013.01)

(58) Field of Classification Search
None
See application file for complete search history.

(56) References Cited

U.S. PATENT DOCUMENTS

| | | | |
|---|---|---|---|
| 4,028,386 A | 6/1977 | Hainaut et al. |
| 4,169,157 A | 9/1979 | Kijima et al. |
| 7,700,654 B2 * | 4/2010 | Hoffmann ............ A61K 36/736 514/604 |

FOREIGN PATENT DOCUMENTS

| | | |
|---|---|---|
| EP | 0302436 A2 | 2/1989 |
| EP | 1471052 A1 | 10/2004 |

(Continued)

OTHER PUBLICATIONS

Dong et al, Organic Letters (2010), 12(5), 1068-1071.*
Xu et al., Tetrahedron Letters (1994), 35 (16), 2495-8. ( CAS Abstract Only).*
International Search Report in corresponding International Patent Application No. PCT/NL2012/050262, mailed Jan. 23, 2013.
Appendino, G., et al., "A Regioselective Synthesis of 3-Isoprenyl-4-Hydroxycoumarins," *Synthetic Communications*, vol. 22, No. 15, pp. 2205-2212 (1992).
Armstrong, Rosemary J., et al., "Synthesis of (±)-karahana ether and a (±)-labdadienoic acid by the electrophilic cyclization of epoxy allylsilanes," *Canadian Journal of Chemistry*, vol. 64, pp. 584-596 (1986).
Baker, Raymond, et al., "Reactions of Active Methylene and Carbonyl Compounds With Myrcene Catalysed by Palladium and Nickel Complexes," *Tetrahedron Letters*, vol. 38, pp. 3575-3578 (1978).

(Continued)

*Primary Examiner* — Kamal Saeed
(74) *Attorney, Agent, or Firm* — Leydig, Voit & Mayer, Ltd.

(57) ABSTRACT

The invention relates to novel therapeutic compounds, more in particular to biologically active analogs and uses thereof as medicament, for instance for the treatment of atrial fibrillation. Provided is a compound of the general formula (formula I) wherein $R_1$ is H or a saturated or unsaturated aliphatic moiety comprising 1 to 8 C-atoms; and X is selected from the group consisting of moieties $X_1$, $X_2$, $X_3$, $X_4$, $X_5$ and $X_6$. Exemplary uses include the prevention or therapeutic treatment of a HSF1-mediated disease.

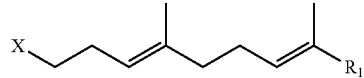

(I)

8 Claims, 4 Drawing Sheets

Figure 1:
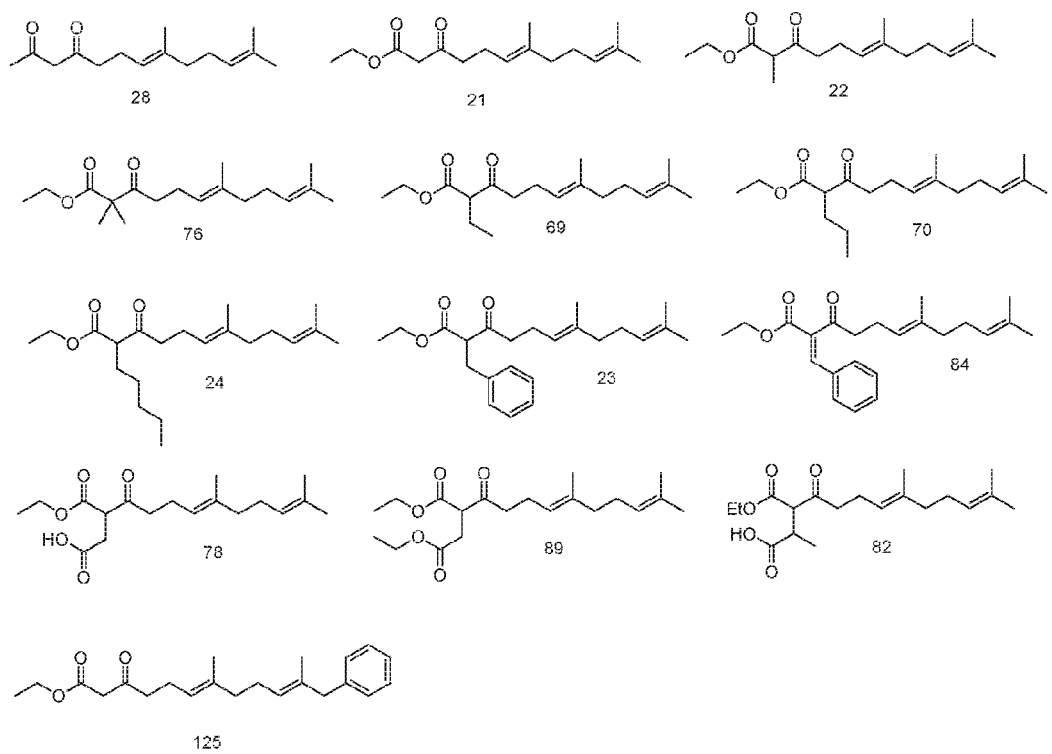

(51) Int. Cl.
*C07C 233/91* (2006.01)
*C07C 237/06* (2006.01)
*C07C 237/22* (2006.01)

(56) References Cited

FOREIGN PATENT DOCUMENTS

| GB | 838569 | 6/1960 |
|----|--------|--------|
| JP | 55-136250 A | 10/1980 |
| WO | WO 2006/062402 A2 | 6/2006 |
| WO | WO 2012/026813 A2 | 3/2012 |

OTHER PUBLICATIONS

Booth, Paul M., et al., "Preparation of Acyltetronic Acids using t-Butyl Acetothioacetate: Total Synthesis of the Fungal Metabolites Carolic, Carlosic, and Carlic Acids," *Journal of the Chemical Society, Perkin Transactions 1*, pp. 121-129 (1987).
Brundel, Bianca J.J.M., et al., "Heat shock proteins as molecular targets for intervention in atrial fibrillation," *Cardiovascular Research*, vol. 78, pp. 422-428 (2008).
Brundel, Bianca J.J.M., et al., "Induction of Heat Shock Response Protects the Heart Against Atrial Fibrillation," *Circulation Research*, vol. 99, pp. 1394-1402 (Dec. 8/22, 2006).
Brundel, Bianca J.J.M., et al., "Heat shock protein upregulation protects against pacing-induced myolysis in HL-1 atrial myocytes and in human atrial fibrillation," *Journal of Molecular and Cellular Cardiology*, vol. 41, pp. 555-562 (2006).
Durst, H. Dupont, et al., "Phase Transfer Catalysis. The Acetoacetic Ester Condensation," *The Journal of Organic Chemistry*, vol. 39, No. 22, pp. 3271-3273 (1974).
Fung, Anthony K.L. et al., "(1α,2β,3β,4α)-1,2-Bis[N-propyl-N-(4-phenoxybenzyl)amino]carbonyl]cyclobutane-3,4-dicarboxylic Acid (A-87049): A Novel Potent Squalene Synthase Inhibitor," *Journal of Medicinal Chemistry*, vol. 40, pp. 2123-2125 (1997).
Hirakawa, Tetsuya, et al., "Geranylgeranylacetone Induces Heat Shock Proteins in Cultured Guinea Pig Gastric Mucosal Cells and Rat Gastric Mucosa," *Gastroenterology*, vol. 111, pp. 345-357 (1996).
Katsuno, Masahisa, et al., "Pharmacological induction of heat-shock proteins alleviates polyglutamine-mediated motor neuron disease," *Proceedings of the National Academy of Sciences of the United States*, vol. 102, No. 46, pp. 16801-16806 (Nov. 15, 2005).
Neipp, Christopher E., et al., "The Synthesis of Homoallylic Amines Utilizing a Cuprate-Based 1,2-Metalate Rearrangement," *The Journal of Organic Chemistry*, vol. 66, pp. 531-537 (2001).
Okochi, Tornoko, et al., "New Enantioselective Synthesis of (10R,11S)-(+)-Juvenile Hormones I and II," *European Journal of Organic Chemistry*, pp. 2145-2150 (2001).
Prasad, Mahavir, "Amidinium Cation as a Mimic of Allylic Carbocation: Synthesis and Squalene Synthetase Inhibitory Activity of an Amidinium Analog of a Carbocation Intermediate," *Journal of Medicinal Chemistry*, vol. 36, pp. 631-632 (1993).
Sakabe, Masao, et al., "Effects of a heat shock protein inducer on the atrial fibrillation substrate caused by acute atrial ischaemia," *Cardiovascular Research*, vol. 78, pp. 63-70 (2008).
Sanbe, Atsushi, et al., "Protective Effect of Geranylgeranylacetone via Enhancement of HSPB8 Induction in Desmin-Related Cardiomyopathy," *PLoS One*, vol. 4, No. 4, e5351, pp. 1-11 (Apr. 2009).
Shimizu, Isao, et al., "Facile Allylation of Ethyl 4,4,4-Trifluoroacetoacetate by Palladium Catalysis," *Synlett*, pp. 301-302 (Apr. 1992).
Shirakabe, Hikoo, et al., "Clinical Evaluation of Teprenone, A Mucosal Protective Agent, in the Treatment of Patients with Gastric Ulcers: A Nationwide, Multicenter Clinical Study," *Clinical Therapeutics*, vol. 17, No. 5, pp. 924-935 (1995).
Suhara, Yoshitomo, et al., "Design and synthesis of biologically active analogues of vitamin $K_2$: Evaluation of their biological activities with cultured human cell lines," *Bioorganic & Medicinal Chemistry*, vol. 16, pp. 3108-3117 (2008).
Xu, Daqiang, et al., "Study of the Regio- and Enantioselectivity of the Reactions of Osmium Tetroxide with Allylic Alcohols and Allylic Sulfonamides," *Tetrahedron Letters*, vol. 35, No. 16, pp. 2495-2498 (1994).
Yoshikawa, Naoyuki, et al., "Isoprenoid geranylgeranylacetone inhibits human colon cancer cells through induction of apoptosis and cell cycle arrest," *Anti-Cancer Drugs*, vol. 21, pp. 850-860 (2010).
Zakarian, Joseph E., et al, "Exploiting Quadrupolar Interactions in the Synthesis of the Macrocyclic Portion of Longithorone C," *Organic Letters*, vol. 10, No. 14, pp. 2927-2930 (2008).
Zhang, Deli, et al., "Effects of different small HSPB members on contractile dysfunction and structural changes in a *Drosophilia melanogaster* model for Atrial Fibrillation," *Journal of Molecular and Cellular Cardiology*, vol. 51, pp. 381-389 (2011).

\* cited by examiner

A

B

GERANYL GERANYL ACETONE ANALOGS AND USES THEREOF

The invention relates to novel therapeutic compounds, more in particular to biologically active, truncated analogs of geranylgeranylacetone (GGA), uses of the analogs and to methods for providing them.

GGA is an acyclic polyisoprenoid that has been used to protect gastric mucosa. The chemical structure of GGA (IUPAC name: (5E,9E,13E)-6,10,14,18-tetramethylnonadeca-5,9,13,17-tetraen-2-one) is as follows:

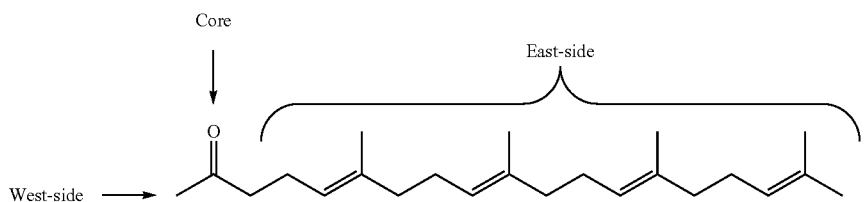 [SMILES: CC(=O)CC/C=C(\C)CC/C=C(\C)CC/C=C(\C)CCC=C(C)C]

GGA is compromised of three parts: a 17 carbon long alkyl chain on the east-side, a carbonyl fragment (ketone) at its core and a west-side terminal methyl group. The hydrophobic, apolar alkyl chain on the east-side consists of four repeating isopropenoid fragments. The trivial name of two such fragments is "geranyl". Three of such consecutive fragments are trivially called "farnesyl" and four isoprepenoids are referred to as "geranylgeranyl". The core is a slightly polarized C=O bond with a small positive charge on the carbon and a small negative charge on the oxygen. The oxygen of ketones can act as a hydrogen bond acceptor.

GGA has been shown to activate transcription factors, particularly heat shock transcription factor (HSF)-1, which are able to bind to DNA and induce transcription. HSF-1 is normally suppressed since it is typically bound to the C-domain of constitutively active HSP70. Since the 1980s GGA, also known as teprenone, is marketed as an anti-ulcer drug in Japan under the commercial name Selbex. It is widely used and appears to be non-toxic. U.S. Pat. No. 4,169,157 discloses GGA and GGA-derivatives and their use in treating peptic ulcers. Recent investigation revealed novel potential of this agent as a general cytoprotective compound. For example, GGA eased ischemic brain injury, endotoxin shock, atrial fibrillation, showed anti-inflammatory potential and could procure potential therapeutic advantages in the prevention and treatment of ischemia/reperfusion disorders, injury, inflammation, infection and organ transplants. Several patents claim the use of GGA in the treatment of glaucoma, hepatitis C, dermatosis or as a topical anti-aging active substance.

In the majority of cases the effect of GGA is ascribed to its heat shock protein inducing ability. Whereas especially the relationship between GGA and the 70-kDa heat shock protein HSP72 is well-established, effects mediated by small heat shock proteins such as HSP27 are also reported. For example, WO2006/062402 discloses that GGA can increase the amount of HSP27 or a HSP27-like protein in a cardiac cell, providing for the use of GGA for manufacture of a medicament for the treatment of a supraventricular arrhythmia e.g., atrial fibrillation.

The present inventors set out to propose rational modifications of GGA in an attempt to obtain novel drugs, for instance for the treatment or prevention of atrial fibrillation.

A further aim was to provide novel biologically active compounds that can be synthesized in an economical fashion.

Surprisingly, the above goals were met by the identification of biologically active derivatives/bioisosters of GGA having a truncated terpenoid structure comprising only two instead of isoprenoid fragments and wherein the ketone core is replaced by a bioisoster. The analogs are herein referred to as geranyl geranyl acetone (GGA) analogs.

In one aspect, the invention relates to a compound of the general formula I

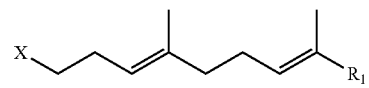

wherein
$R_1$ is H or a saturated or unsaturated aliphatic moiety comprising 1 to 8 C-atoms and wherein X is selected from the group consisting of moieties $X_1$, $X_2$, $X_3$, $X_4$, $X_5$ and $X_6$ as defined herein below. Also encompassed are pharmaceutically acceptable salts and isomers of the compounds.

In another embodiment, $R_1$ is a $C_1$-$C_6$-alkyl, like $CH_3$, phenyl, benzyl or cycloalkyl. Preferably, $R_1$ comprises a 5- or 6-membered cycle, such as benzyl. In one aspect, $R_1$ is $CH_2$—$C_6H_5$.

$X_1$ has the formula

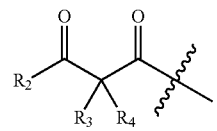

wherein $R_2$ is H, $C_1$-$C_5$ alkyl, $C_1$-$C_5$ alkoxy, $C_1$-$C_5$ aminoalkyl or $C_1$-$C_5$ thioalkyl, optionally substituted with one or more selected from the group consisting of halogen, oxo, nitro, carboxylic acid/ester, hydroxyl, —CN, alkoxy, amino, amido, aryl, substituted aryl, hetero-aryl, substituted heteroaryl, cyclo-alkyl and heterocycloalkyl.

$R_3$ and $R_4$ are independently selected from H; $C_1$-$C_5$ alkyl, optionally substituted with one or more of halogen, oxo, hydroxyl, —CN, alkoxy, amino, amido, aryl; substituted aryl; hetero-aryl; substituted heteroaryl; cyclo-alkyl; heterocycloalkyl; nitro; carboxylic acid/ester; —$CH_2$—C(=O)O—R3a and —$CHCH_3$— C(=O)O—R3a, wherein R3a is H or C1-C6 alkyl. Alternatively, $R_3$ and $R_4$ together form a substituted or non-substituted =C(H)— aryl, a substituted or non-substituted =C(H)-heteroaryl, or a substituted or non-substituted =C(H)—$C_1$-$C_5$ alkyl.

$X_2$ has the formula

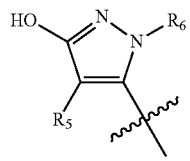

wherein R5 and R6 are independently selected from H and $C_1$-$C_5$ alkyl, optionally substituted with one or more selected from the group consisting of halogen, oxo, hydroxyl, —CN, alkoxy, amino, amido, aryl, substituted aryl, hetero-aryl, substituted hetero-aryl, cyclo-alkyl, heterocycloalkyl, nitro, and carboxylic acid/ester.

$X_3$ has the formula

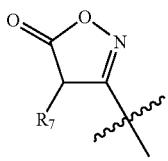

wherein R7 is H or a $C_1$-$C_5$ alkyl group, optionally substituted with one or more selected from the group consisting of halogen, oxo, hydroxyl, —CN, alkoxy, amino, amido, aryl, substituted aryl, hetero-aryl, substituted hetero-aryl, cyclo-alkyl, heterocycloalkyl, nitro, carboxylic acid/ester $X_4$ has the formula

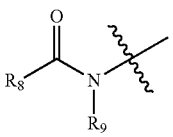

wherein R8 and R9 are independently selected from the group consisting of H, Y and —C(═O)—Y, wherein Y is a $C_1$-$C_5$ alkyl group, an N-linked $C_1$-$C_5$ alkyl group, a 5- or 6-membered (hetero)aromatic group or an N-linked 5- or 6-membered (hetero)aromatic group, optionally substituted with one or more selected from the group consisting of halogen, oxo, sulfoxide, sulfonate, hydroxyl, —CN, alkoxy, amino, nitro, aryl, substituted aryl, hetero-aryl, substituted hetero-aryl, cyclo-alkyl, heterocycloalkyl, nitro, carboxylic acid/ester. Preferably, $R_8$ is not $CF_3$.

$X_5$ has the formula

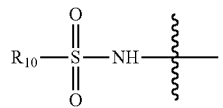

wherein $R_{10}$ is a $C_1$-$C_5$ alkyl group or a 5- or 6-membered (hetero)aromatic group or, optionally substituted with one or more selected from the group consisting of halogen, oxo, sulfo, hydroxyl, —CN, alkoxy, amino, amido, aryl, substituted aryl, hetero-aryl, substituted hetero-aryl, cyclo-alkyl, heterocycloalkyl, nitro, carboxylic acid/ester $X_6$ has the formula

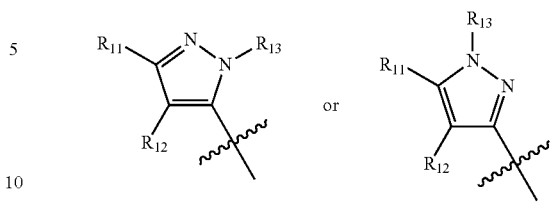

wherein $R_{11}$, $R_{12}$ and $R_{13}$ are independently selected from the group consisting of H, $C_1$-$C_5$ alkyl groups and 5- or 6-membered (hetero)aromatic groups, optionally substituted with one or more selected from the group consisting of halogen, oxo, sulfo, hydroxyl, —CN, alkoxy, amino, amido, aryl, substituted aryl, hetero-aryl, substituted hetero-aryl, cyclo-alkyl, heterocycloalkyl, nitro, carboxylic acid/ester In one embodiment, the invention provides a compound of the general formula I wherein X is $X_1$, and wherein $R_2$, $R_3$ and $R_4$ are as defined above.

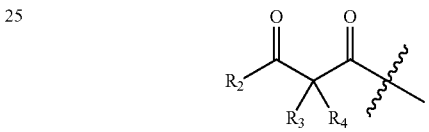

For example, $R_2$ is H or $C_1$-$C_5$ alkoxy, optionally substituted with one or more selected from the group consisting of halogen, oxo, hydroxyl, —CN, alkoxy, amino, amido, aryl, substituted aryl, hetero-aryl, substituted hetero-aryl, cyclo-alkyl, heterocycloalkyl, nitro, carboxylic acid/ester. In one aspect, R2 is suitably selected from —$OCH_3$, —$OC_2H_5$ and —$OC_3H_7$. See for example compound 21, 22, 76, 69, 70, 71, 23, 24, 84, 78, 89 or 125. In a specific aspect, $R_2$ is $OC_2H_5$ and $R_1$ is H or benzyl (e.g. compound 125). In another embodiment, $R_2$ is H or $C_1$-$C_5$ alkyl, preferably $C_1$-$C_3$ alkyl, more preferably —$CH_3$ or H (e.g. compound 28), optionally in combination with $R_1$ is H.

$R_3$ and $R_4$ are independently selected from H and $C_1$-$C_5$ alkyl, optionally substituted with one or more of halogen, oxo, hydroxyl, —CN, alkoxy, amino, amido, phenyl, benzyl, hetero-aryl, cyclo-alkyl, heterocycloalkyl, —C(═O)O— R3a, wherein R3a is H, $C_1$-$C_6$ alkyl. Alternatively, $R_3$ and $R_4$ together form a substituted or non-substituted ═C(H)-aryl, a substituted or non-substituted ═C(H)-heteroaryl, or a substituted or non-substituted ═C(H)—$C_1$-$C_5$ alkyl.

In one aspect, at least one of $R_3$ and $R_4$ is H. For instance, provided is a compound wherein $R_1$ is H, $R_2$ is $OC_2H_5$, and at least one of $R_3$ and $R_4$ is H. In another aspect, at least one of $R_3$ and $R_4$ is an unsubstituted $C_1$-$C_5$ alkyl or a $C_1$-$C_5$ alkyl substituted with one or more, preferably one, of halogen, oxo, hydroxyl, —CN, alkoxy, amino, amido, phenyl, benzyl, hetero-aryl, cyclo-alkyl, heterocycloalkyl, (compound 22, 76, 69, 70, 71, 14) or $CH_2$-aryl (compound 23).

$R_3$ and/or $R_4$ may be a $C_1$-$C_5$ alkyl, optionally substituted with one or more of —C(═O)O—R3a, wherein R3a is H or $C_1$-$C_6$ alkyl. For instance, $R_3$ or $R_4$ is —$CH_2$C(═O)OH, —CH($CH_3$)C(═O)OH, —$CH_2$C(═O)O—$C_1$-$C_6$ alkyl. (e.g. compounds 82, 78, 89)

In still a further aspect, $R_3$ and $R_4$ together form a ═C(H)-aryl, ═(H)-heteroaryl or ═C(H)—$C_1$-$C_5$ alkyl. For example, $R_3$ and $R_4$ together form ═C(H)$C_6H_5$. Exemplary compounds wherein X is $X_1$ are depicted in FIG. 1. Preferred compounds include compounds 21, 23, 28, 76, 78, and 89.

In a further embodiment, a compound is provided wherein X is $X_2$, $X_2$ having the formula

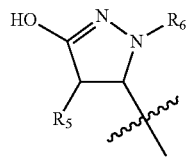

wherein $R_5$ and $R_6$ are independently selected from H and $C_1$-$C_5$ alkyl, optionally substituted with one or more selected from the group consisting of halogen, oxo, hydroxyl, —CN, alkoxy, amino, amido, aryl, substituted aryl, hetero-aryl, substituted hetero-aryl, cyclo-alkyl, heterocycloalkyl, nitro and carboxylic acid/ester.

Figure 2:
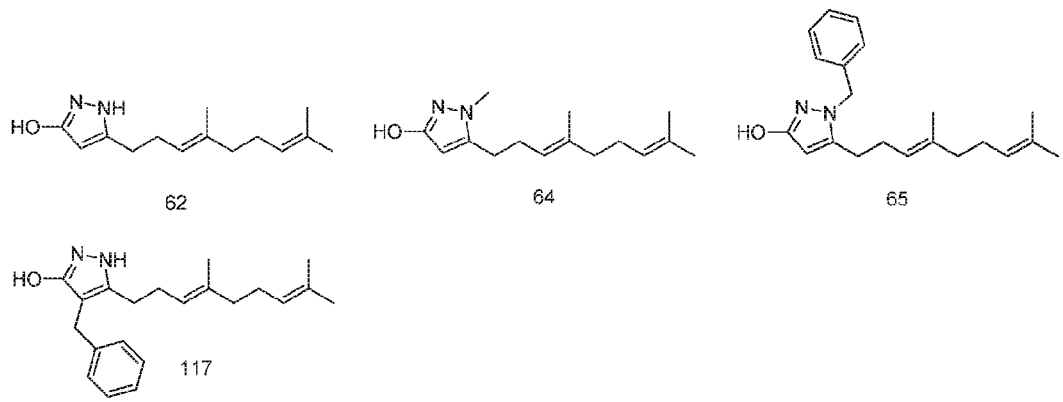

In one embodiment, at least one of $R_5$ and $R_6$ is H (e.g. compounds 62, 64, 65, 117). For example, $R_5$ is H, $R_6$ is H or both $R_5$ and $R_6$ are H. At least one of $R_5$ and $R_6$ can be a $C_1$-$C_5$ alkyl, optionally substituted with one or more of halogen, oxo, hydroxyl, —CN, alkoxy, amino, amido, phenyl, benzyl, hetero-aryl, cyclo-alkyl and heterocycloalkyl. In a specific aspect, $R_5$ and/or $R_6$ is a $C_1$-$C_3$ alkyl, optionally substituted with a phenyl. In another specific aspect, $R_5$ is H and $R_6$ is H or unsubstituted $C_1$-$C_5$ alkyl, preferably $C_1$-$C_3$ alkyl. Exemplary compounds wherein X is $X_2$ are depicted in FIG. 2. Preferred compounds include compounds 62 and 64.

In a further embodiment, a compound is provided wherein X is $X_3$, $X_3$ having the formula

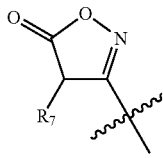

wherein $R_7$ is H or a $C_1$-$C_5$ alkyl group, optionally substituted with one or more selected from the group consisting of halogen, oxo, hydroxyl, —CN, alkoxy, amino, amido, aryl, substituted aryl, hetero-aryl, substituted hetero-aryl, cyclo-alkyl, heterocycloalkyl, nitro and carboxylic acid or carboxylic ester.

Preferably, $R_7$ is H or an unsubstituted $C_1$-$C_3$ alkyl. For example, provided is compound 111 (see FIG. 3).

In still a further embodiment, a compound is provided wherein X is $X_4$, $X_4$ having the formula

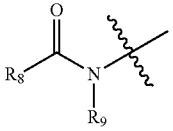

wherein $R_8$ and $R_9$ are independently selected from the group consisting of H, Y and —C(=O)—Y, wherein Y is a $C_1$-$C_5$ alkyl group, N-linked $C_1$-$C_5$ alkyl group, 5- or 6-membered (hetero)aromatic group or N-linked 5- or 6-membered (hetero)aromatic group, optionally substituted with one or more selected from the group consisting of halogen, oxo, sulfoxide, sulfonate, hydroxyl, —CN, alkoxy, amino, nitro, carboxylic acid and carboxylic ester; or wherein $R_8$ and $R_9$ together form a structure —$(CH_2)_n$— or —$(CH_2)_n$—C(O)—, wherein n=2-4, optionally substituted with one or more selected from the group consisting of halogen, oxo, sulfoxide, sulfonate, hydroxyl, —CN, alkoxy, amino, nitro, carboxylic acid and carboxylic ester.

In one embodiment, at least one of $R_8$ and $R_9$ is H. In one preferred aspect, $R_9$ is H and $R_8$ is selected from the group consisting of H, $C_1$-$C_5$ alkyl groups, N-linked straight chain $C_1$-$C_5$ alkyl groups, 5- or 6-membered (hetero)aromatic groups, and N-linked 5- or 6-membered (hetero)aromatic groups, optionally substituted with one or more selected from the group consisting of halogen, oxo, sulfoxide, sulfonate, hydroxyl, —CN, alkoxy, amino, nitro, carboxylic acid, ester. For example, $R_9$ is H and $R_8$ is selected from the group consisting of $C_1$-$C_5$ alkyl groups and 5- or 6-membered (hetero)aromatic groups, optionally substituted with one or more of halogen, oxo, sulfo, hydroxyl, —CN, alkoxy, amino, amido, phenyl, benzyl, hetero-aryl, cyclo-alkyl and heterocycloalkyl. Exemplary compounds include 43, 4649, 56, 91, 98 and 101 (see FIG. 4). As another example, $R_9$ is H and $R_8$ is selected from the group consisting of N-linked straight chain $C_1$-$C_5$ alkyl groups and N-linked 5- or 6-membered (hetero)aromatic groups, optionally substituted with one or more selected from the group consisting of halogen, oxo, sulfoxide, sulfonate, hydroxyl, —CN, alkoxy, amino, nitro, carboxylic acid, ester. Exemplary compounds include compounds 44 and 45.

A further aspect relates to compounds wherein X is $X_4$ and wherein at least $R_9$ is selected from the group consisting of Y and —C(=O)—Y, wherein Y is a $C_1$-$C_5$ alkyl group, N-linked $C_1$-$C_5$ alkyl group, 5- or 6-membered (hetero) aromatic group or N-linked 5- or 6-membered (hetero) aromatic group, optionally substituted with one or more selected from the group consisting of halogen, oxo, sulfoxide, sulfonate, hydroxyl, —CN, alkoxy, amino, nitro, carboxylic acid, ester, preferably in combination with $R_8$ being an unsubstituted $C_1$-$C_3$ alkyl (e.g. 103, 127 or 128).

In a specific aspect, $R_8$ and $R_9$ together form a structure —$(CH_2)_n$— or —$(CH_2)_n$—C(O)—, wherein n=2-4, optionally substituted with one or more selected from the group consisting of halogen, oxo, sulfoxide, sulfonate, hydroxyl, —CN, alkoxy, amino, nitro, carboxylic acid and carboxylic ester. Preferably, $R_8$ and $R_9$ together form a structure —$(CH_2)_n$—C(O)— wherein n is 2 or 3. See for example compound 47.

The invention also provides a compound of the general formula I wherein X has the formula

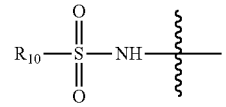

wherein $R_{10}$ is a $C_1$-$C_5$ alkyl group or a 5- or 6-membered (hetero)aromatic group or, optionally substituted with one or more selected from the group consisting of halogen, oxo, sulfo, hydroxyl, —CN, alkoxy, amino, amido, aryl, substituted aryl, hetero-aryl, substituted hetero-aryl, cyclo-alkyl, heterocycloalkyl, nitro, carboxylic acid and carboxylic ester. Preferably, $R_1$ is H. In one embodiment, $R_{10}$ is a $C_1$-$C_5$ alkyl, optionally substituted with one, two or three halogen substituents, for example trifluoromethyl (e.g. compounds 51 and 52). In another embodiment, $R_{10}$ is a substituted or unsubstituted aromatic moiety, for instance a benzyl moiety (53).

Yet a further aspect of the present invention relates to GGA-analogs according to Formula I wherein X is $X_6$, $X_6$ having the formula

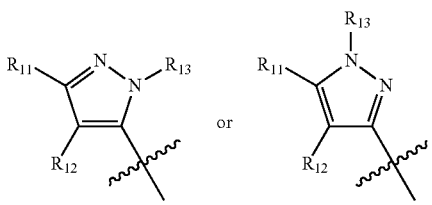

wherein $R_{11}$, $R_{12}$ and $R_{13}$ are independently selected from the group consisting of H, $C_1$-$C_5$ alkyl groups and 5- or 6-membered (hetero)aromatic groups, optionally substituted with one or more selected from the group consisting of halogen, oxo, sulfo, hydroxyl, —CN, alkoxy, amino, amido, aryl, substituted aryl, hetero-aryl, substituted hetero-aryl, cyclo-alkyl, heterocycloalkyl, nitro, carboxylic acid/ester. As can be seen, the structures represent tautomers.

In one embodiment, at least one of $R_{11}$, $R_{12}$ and $R_{13}$ is H. R11 may be $C_1$-$C_3$ alkyl, such as methyl. In a specific aspect, $R_{11}$ is methyl, $R_{12}$ is H and $R_{13}$ is a $C_1$-$C_5$ alkyl group or a 5- or 6-membered (hetero)aromatic group, optionally substituted with one or more of halogen, oxo, sulfo, hydroxyl, —CN, alkoxy, amino, amido, phenyl, benzyl, hetero-aryl, cyclo-alkyl and heterocycloalkyl. As an example, $R_{13}$ is a substituted alkyl group, for instance —(CH$_2$)nCN or —(CH$_2$)$_n$OH wherein n is 1-5, preferably 1-3. As another example, $R_{13}$ is a mono-substituted benzyl- or phenyl-group, like —(CH$_2$)—C$_6$H$_4$F or —(CH$_2$)—C$_6$H$_4$CN. Preferably, the substituent is in the ortho-position on the phenyl-ring (e.g. compound 40).

Figure 6:
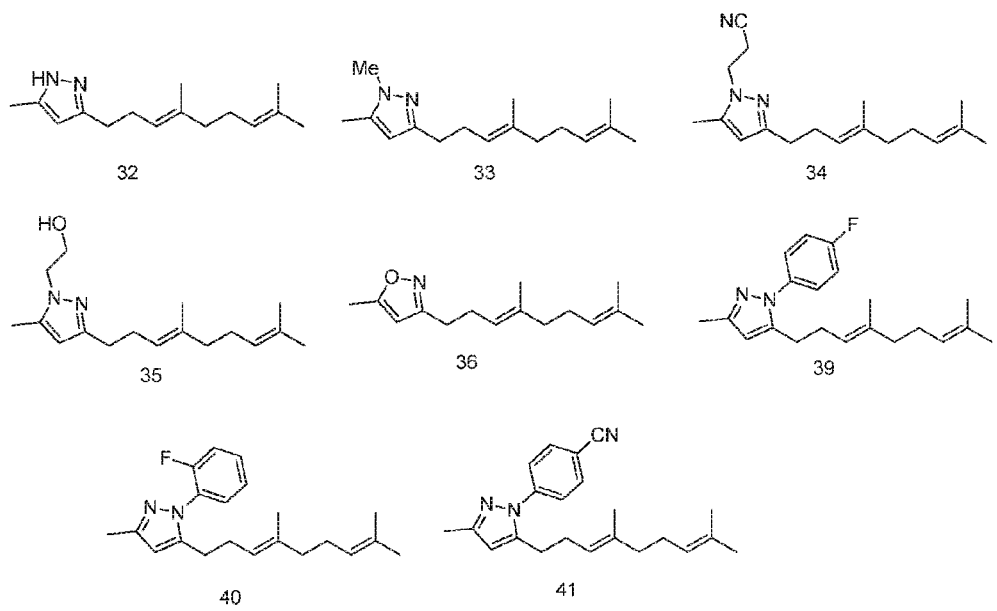

Exemplary compounds wherein X is $X_6$ are depicted in FIG. 6. Preferred compounds include compounds 32, 33, 35 and 40.

In still a further aspect, the invention provides a compound of the general Formula II Formula II

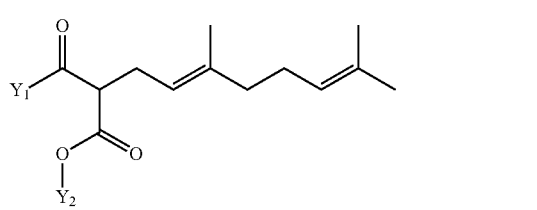

wherein $Y_1$ is selected from the group consisting of H, $C_1$-$C_5$ alkyl groups and 5- or 6-membered (hetero)aromatic groups, optionally substituted with one or more selected from the group consisting of halogen, oxo, sulfo, hydroxyl, —CN, alkoxy, amino, amido, aryl, substituted aryl, hetero-aryl, substituted hetero-aryl, cyclo-alkyl, heterocycloalkyl, nitro, carboxylic acid and carboxylic ester; and wherein $Y_2$ is H or a $C_1$-$C_3$ alkyl chain, or a pharmaceutically acceptable salt thereof.

Preferably, $Y_1$ is $C_1$-$C_3$ alkyl, more preferably methyl (e.g. compound 81) or a 5- or 6-membered (hetero)aromatic group, optionally substituted with one or more selected from the group consisting of halogen, oxo, sulfo, hydroxyl, —CN, alkoxy, amino, amido and aryl. For example, $Y_1$ is a phenyl moiety comprising at least a substituent at the ortho-position, for instance a hydroxyl or halogen. Preferably, $Y_2$ is —CH$_3$ or C$_2$H$_5$.

Figure 7:
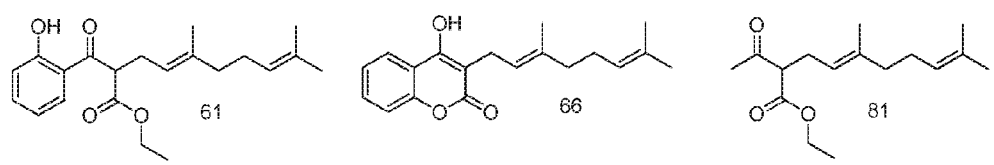

In a specific aspect, the compound is compound 61 or 81 as depicted in FIG. 7. Also provided is the tautomeric structure represented by compound 66 (FIG. 7)

In still a further aspect, the invention provides compound 106 having the formula

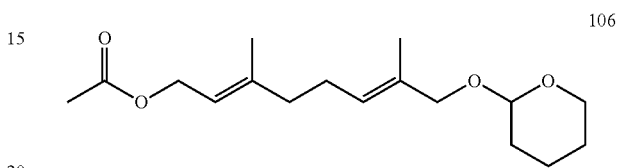

or a pharmaceutically acceptable salt thereof.

The invention also provides a method for the synthesis of a compound of the invention. General methods known in the art can be applied using commercially available precursors. Depending on the structure of the desired compound, the skilled person will be able to select the appropriate routes and starting materials. See Example 1 for exemplary embodiments.

GGA-like compounds were screened for HSP70 boosting effects. Hereto, HL-1 cardiomyocytes were first subjected to a mild heat shock which activates the Heat Shock Factor. After the mild heat shock, compound (10 μM) was added to the medium of HL-1 cardiomyocytes followed by determination of the HSP70 amount. We observed that GA analogues are strong inducers of HSP70 expression (see Table 1).

Therefore, a GGA-analog may be used to induce a heat shock protein. Heat shock proteins (HSPs) function as molecular chaperones to prevent protein aggregation and facilitate the folding of non-native proteins, particularly new peptides emerging from ribosomes. Molecular chaperones recognize non-native proteins, predominantly via exposed hydrophobic residues, and bind selectively to those proteins to form relatively stable complexes. In these complexes, the protein is protected and able to fold into its native form. HSPs show increased levels of expression when cells are subjected to elevated temperatures and other metabolic stresses. Examples of metabolic stresses which elicit elevated expression of heat shock proteins include: decreased glucose availability; increased intercellular calcium levels; and decreased blood flow, in particular ischemia/reperfusion conditions. In a preferred aspect, a compound of the invention finds its use in modulating heat shock factor 1 (HSF1) dependent expression of a heat shock protein, in particular HSP70 and relatives thereof. In fact, a compound as disclosed herein may be seen as HSF modulator, in particular as HSF activator.

A compound of the invention finds its use among others in various therapeutic applications, including those known for GGA. Thus, also provided is a compound as defined herein above as medicament. Also provided is a pharmaceutical composition comprising at least one GGA-like compound as disclosed herein, together with a pharmaceutically acceptable excipient, carrier or diluent. Also provided is a GGA-like compound as disclosed herein for use in a method of prophylactic and/or therapeutic treatment of a disease or disorder. Exemplary diseases and disorders include gastric ulcers, ischemic brain injury, fibrosis of e.g. the lungs, kidneys or liver, endotoxin shock, atrial fibrillation, glaucoma, hepatitis C, dermatosis, ischemia/reperfusion disorders, injury, inflammation, infection and organ transplants, or as a topical anti-aging active substance.

In a preferred aspect, a compound of the invention finds its use in the treatment or prevention of a disease associated with heat shock factor 1 (HSF1) dependent expression of a heat shock protein, in particular HSP70 and relatives thereof like HSP25, HSP90 and HSP40. HSF1-mediated diseases include cystic fibrosis (CF), ALS and gastrointestinal diseases. For example, a compound (HSF mimetic) of in the invention may be used in protecting against both irritant-induced gastric lesions and IBD-related colitis. By inducing Hsp70 expression, a GGA-like compound can protect neurons from protein aggregation and toxicity (Parkinson disease, Alzheimer disease, polyglutamine diseases, and amyotrophic lateral sclerosis). It may protect cells from apoptosis (Parkinson disease) and from inflammation (cerebral ischemic injury).

In a specific aspect, a compound of the invention is used for the treatment or prophylaxis of acute kidney injury conditions (AKI). AKI is common, costly and independently associated with increased risk of death. Patient outcomes are directly related to AKI severity, including even minor changes in serum creatinine. More severe AKI is an independent risk factor for death with mortality rates generally exceeding 30% and often exceeding 50%> when it occurs in the setting of trauma, surgery or multiple organ dysfunction. After acute injury, tubular epithelial cells die through both necrotic and apoptotic mechanisms, and cells that survive the insult dedifferentiate and proliferate to reconstitute a functioning nephron. Strategies to increase the fraction of epithelial cells that survive the initial insult should be therapeutic, by providing a larger mass of epithelial progenitors during the repair phase. Acute kidney injury remains a major health problem with few therapeutic options. Accordingly, there is a considerable need for new therapies and therapeutic agents that are effective for the treatment of AKI. As is shown in Example 3 herein below, it was found that at exemplary compounds 32, 46, 47, 49, 51, 52, 61, 62, 69, 95 and 106 were strong inducers of Hsp70 expression in renal cells. Since Hsp70 induction is known to provide protection against renal injury, in particular ischemic injury, these findings demonstrate that an analog of the present invention is suitably used in the management of AKI, for instance by protecting kidney tubular cells from apoptosis.

Provided is a method of preventing or treating an acute kidney injury in a subject in need thereof, comprising administering to the subject an effective amount of a GGA-like compound. Preferably, the subject is a human subject. As used herein, the terms "treat," "treating," or "treatment," mean to counteract an AKI to the extent that the AKI is improved according to a clinically-acceptable standard. An improvement in an acute kidney injury can be determined according to one or more of the following clinical standards: 1) reduction in serum creatinine, 2) increase in kidney function, 3) increase in urine output, 4) decrease in blood urea nitrogen. Other markers such as the expression levels of Nur77 can be used. Clinical improvement in AKI can also be determined using one or more alternate biomarkers.

Also provided is a method of inhibiting apoptosis in kidney epithelial cells after acute injury by exposing the cells to one or more analogs as provided herein. For example, the kidney cells are proximal tubule epithelial cells. The acute injury can be hypoxia-induced injury or an ischemic injury. In one embodiment, the acute kidney injury is a toxicant-induced injury or a septic injury. Preferred analogs for use in AKI therapy include compounds 32, 46, 47, 49, 51, 52, 61, 62, 69, 95 and 106. The GGA-like compound(s) may be administered in combination with one or more therapies, e, g, selected from the group consisting of vasodilation, volume replacement, blood purification and renal replacement therapy and/or therapeutic agents useful for preventing or treating AKI, including diuretics, antibiotics, calcium and glucose/insulin.

Still further, e.g. via HSP induction, a compound provided herein can have an adjuvant role in antigen presentation and it may be involved in the immune response in autoimmune disease (multiple sclerosis).

In one embodiment, a compound of the invention is used in the treatment and/or prevention of a disease which is associated with the accumulation of misfolded proteins, for example supraventricular arrhythmia, preferably atrial fibrillation (AF). Repetitive, forceful muscular contractions, i.e. physical exercise, cause changes in the expression patterns of genes and proteins. These changes can result in muscle adaptations such as muscle atrophy via muscle protein catabolism or muscle hypertrophy via muscle protein accretion. During hypertrophy, numerous nascent proteins are formed. An increase in the presence of molecular chaperones, like HSPs, will act to enhance the stability of these nascent proteins until they can fold into their native forms. Thus, compounds disclosed herein also find their use in situations of enhanced protein turnover, such as the environment in muscle following exercise; it would be advantageous for an individual to have a means of increasing the stability of rapidly forming proteins in order to reduce the catabolism of these new non-native state proteins.

In one aspect, the invention provides the use of a compound of the general formula I or II for the induction of a heat shock protein, for example in the treatment and/or prophylaxis of a disease which is associated with the occurrence and/or accumulation of misfolded proteins. Diseases associated with the occurrence and/or accumulation of misfolded proteins include prion-related illnesses such as Creutzfeldt-Jakob disease, bovine spongiform encephalopathy (mad cow disease), amyloid-related illnesses such as Alzheimer's disease and familial amyloid cardiomyopathy or polyneuropathy, as well as neurodegenerative diseases, including Alzheimer's disease, Parkinson's disease, amyotrophic lateral sclerosis and Huntington's disease.

In one embodiment, the invention provides the use of a compound of the general formula I or II as disclosed herein for the induction of a heat shock protein, for example in the treatment and/or prophylaxis of a disease which is associated with a loss of proteostatic control of the cell, such as the formation and/or accumulation of misfolded or damaged proteins. Combinations of two or more compounds are also envisaged. Exemplary compounds for use in the prophylatic and/or preventive treatment of a disease associated with the accumulation of misfolded proteins include compounds shown in Table 1 to be capable of inducing a heat shock protein, for example compound 23, 70, 76, 78, 84, 89, 61, 62, 64, 28, 79, 32, 33, 35, 44, 46, 49, 51, 52, 53, 56, 91, 100, 103, 105, 106, 60, 95, 97 or 101. In a specific embodiment, the compound induces mammalian HSP70 expression, like compound 23, 76, 61, 62, 28, 46, 49, 51, 52, 60 or 95. Of particular interest are compounds 28, 51, 52, 61, 62 and 76, which are capable of inducing HSP70 protein expression, mammalian HSP mRNA levels and have cardioprotective properties. Also of particular interest are compounds 32, 46, 47, 49, 51, 52, 61, 62, 69, 95 and 106, which are capable of inducing HSP70 protein expression in murine proximal tubule cells (MPT) cells and can protect against renal injury.

Compounds 28, 51, 52, 61, 76, 23, 62, 40, 43 or 128 are of particular interest for the treatment and/or prevention of a disease which is associated with the accumulation of misfolded proteins, for example supraventricular arrhythmia, preferably atrial fibrillation (AF). In one embodiment, the compound is selected from the group consisting of compounds 28, 51, 52, 61 and 76. In another embodiment, the compound is selected from the group consisting of compounds 23, 62, 40, 43 and 128.

Compounds 28, 51, 52, 61, 76, 23, 62, 40, 43 or 128 are also advantageously used in the treatment and/or prevention of a disease which is caused by ischemia or ischemia/reperfusion conditions and is associated with e.g. proteotoxic stress, infiltration of inflammatory cells and apoptosis, for example acute kidney injury after major (cardiac) surgery, post-operative cardiac injury, including post-surgery atrial fibrillation. In one embodiment, the compound is selected from the group consisting of compounds 28, 51, 52, 61 and 76. In another embodiment, the compound is selected from the group consisting of compounds 23, 62, 40, 43 and 128.

Other uses relate to the capacity of GGA-analog to inhibit HSP induction. For example, in cystic fibrosis a cellular HSP response prevents misfolded membrane proteins from being transported to the membrane. However, in some cases the protective HSP response is undesirable because misfolded proteins can still be (partially) functional. A compound of the invention capable of inhibiting or suppressing HSP induction, preferably HSP70, can in such cases advantageously be used. Exemplary compounds include compounds 24, 69, 34, 39, 45, 54, 67, 68, 82, 85 and 98.

Still further uses relate to the cytotoxic and/or pro-apoptotic effects observed for GGA-analogs of the invention. In particular, at least exemplary compounds 41, 45, 65 and 101 were found to induce cell death in a human cancer cell line, presumably via apoptosis (programmed cell death) induction. Accordingly, a GGA-like analog also finds its use in compositions and methods for the (preventive) treatment of a disease associated with unwanted and/or uncontrolled cell proliferation, including treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer and spleen cancer.

The compound according to this invention can be prepared for administration by any conventional process for pharmaceutical preparation. Therefore, this invention provides the pharmaceutical preparations suitable for a medicine for the human body, which comprises at least one of the compounds according to this invention. Such preparations are provided to be administered by a conventional method with any required carrier or excipient for the production of medicine.

The compounds and compositions may, for example, be administered intravascularly, intramuscularly, subcutaneously, intraperitoneally, orally or topically. It will be obvious to those skilled in the art that the following dosage forms may comprise as the active ingredient, either compounds or a corresponding pharmaceutically acceptable salt of a compound. Preferred routes of administration for the GGA-like compounds include oral and intravenous administration. In one embodiment, the compound is administered intravenously by a bolus injection, followed by continuous infusion. In one embodiment, the compound according to this invention is administered orally in a form of powder, tablet, granule, capsule, pill and liquid, or parenterally in injection, suppository and the like. A typical dose amounts of 50-2000 mg of GGA analog per day when used to treat an adult. It is desirable that the dose varies properly depending upon the symptoms and the administration is divided by proper intervals.

The pharmaceutical composition is desirably formulated in a suitable form for absorption from the alimentary canal. The tablet and capsule for oral administration are a form of unit dose, and may contain conventional excipients such as a binder, for example, syrup, gum arabic, gelatine, sorbite, tragacanth gum or polyvinyl pyrolidone; a constituent, for example, lactose, corn starch, calcium phosphate, sorbite of glycine; a lubricant, for example, magnesium stearate, talc, polyethylene glycol or silica; a disintegrator, for example, potato starch; and an acceptable wetting agent, for example, sodium lauryl sulfate. The tablet may be coated by a well-known method in the art. The liquid preparations for oral administration may be an aqueous or oily suspension, solution, syrup, elixir and the like. Alternatively, they may be a dry product which is re-dissolved in water or other suitable vehicle prior to use. Such liquid preparations may contain conventional additives, for example, a suspending agent, such as sorbite syrup, methyl cellulose, glucose/sugar syrup, gelatine, hydroxyethyl cellulose, carboxymethyl cellulose, aluminium stearate gel and hydrogenated edible fat; an emulsifier such as lecithine, sorbitane mono-oleate and gum arabic; a nonaqueous vehicle such as almond oil, fractionated coconut oil, oiliness ester, propylene glycol and ethyl alcohol; an antiseptics such as methyl p-hydroxy benzoate, propyl p-hydroxybenzoate and sorbic acid.

A preparation for injection can be provided in a unit-dose ampoule or vial with an additive antiseptic. The preparations may be a form of suspension, solution or emulsion in an oily or aqueous vehicle, and also may contain a formulating agent such as a suspension agent, stabilizer and/or dispersant. On the other hand, the active ingredient may be a form of powder which is re-dissolved in a suitable vehicle, for example, sterilized water free from exothermic materials, prior to use.

The composition of the present invention may be administered in a dosage form having controlled release characteristics, e.g. time-release. Furthermore, the controlled release may be in forms such as a delayed release of active constituents, gradual release of active constituents, or prolonged release of active constituents. Such active constituents release strategies extend the period of bioavailability or target a specific time window for optimal bioavailability. Advantageously the composition may be administered in the form of a multi-compartment capsule which combines both immediate release and time-release characteristics. Individual components of the composition may be contained in differential compartments of such a capsule such that the specific components may be released rapidly while others are time-dependently released. Alternatively, a uniform mixture of the various components of the present invention may be divided into both immediate release and time-release compartments to provide a multi-phasic release profile.

Also encompassed is a nutritional, neutraceutical or cosmetic composition or supplement comprising a compound according to the invention. According to various embodiments of the present invention, the supplement may be consumed in any form. For instance, the dosage form of the nutritional supplement may be provided as, e.g., a powder beverage mix, a liquid beverage, a ready-to-eat bar or drink product, a capsule, a liquid capsule, a softgel capsule, a tablet, a caplet, or as a dietary gel. The preferred dosage form of the present invention is as a softgel capsule. As used herein, a serving of the present nutritional composition typically comprises from about 1 mg to about 300 mg of a GGA analog of the invention. More preferably, a serving of the present nutritional composition comprises from about 25 mg to about 150 mg, most preferably comprises from about 25 mg to about 75 mg of a GGA-like compound disclosed herein. Additionally, the nutritional supplement set forth in the example embodiment herein may further contain any appropriate number and type of excipients, as is well known in the art.

The present composition or those similarly envisioned by one of skill in the art, may be utilized in therapeutic, prophylactic and/or experimental methods to enhance the expression of heat shock proteins in cells. In one embodiment, the invention provides a method for inducing heat shock protein expression, in particular Hsp70 expression, in a biological sample in vitro, comprising contacting the biological sample with a compound according to the invention. The biological sample may comprise cultured mammalian cells, preferably human cells. A method can for example be used to screen for inhibitors of heat shock protein induction.

Also provided is a method of conducting a drug discovery business comprising i) providing a compound as disclosed herein above, ii) screening the compound for a desired pharmacological activity, iii) optionally modifying the compound to improve its therapeutic profile; and iv) licensing, to a third party, the rights for further drug development of the compound. Modifications may include the conversion of a compound to a pro-drug form which, upon administration to a subject in need thereof, is converted in vivo to a compound having (enhanced) biological activity. Conducting therapeutic profiling may comprise (i) testing for efficacy and toxicity in animals to generate lead compounds; (ii) testing one or more lead compounds for efficacy and/or safety in human subjects, and (iii) formulating and marketing a pharmaceutical preparation including one or more compound having an acceptable therapeutic profile. Such a business method can be further extended by including an additional step of establishing a distribution system for distributing the pharmaceutical preparation for sale, and may optionally include establishing a sales group for marketing the pharmaceutical preparation.

LEGEND TO THE FIGURES

Figure 3:
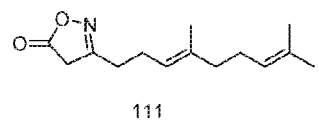
Figure 4:
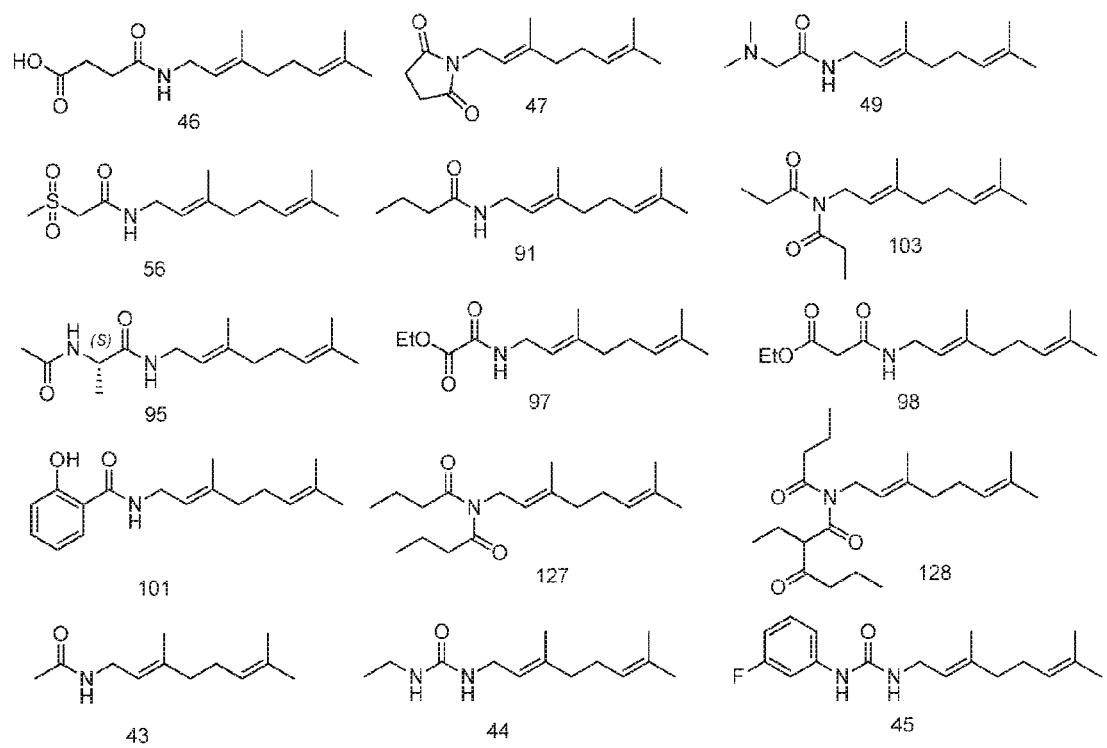
Figure 5:
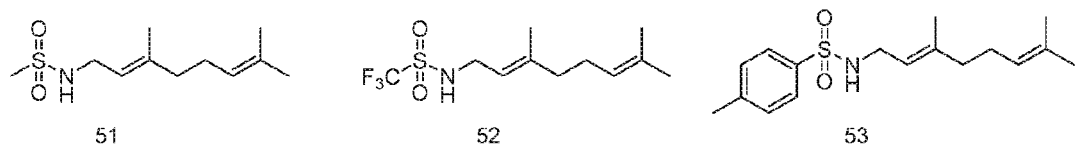
Figure 8:
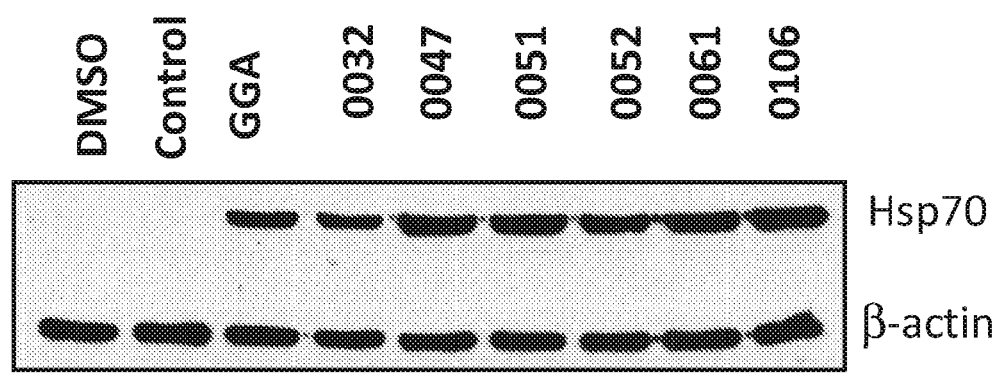
Figure 8:
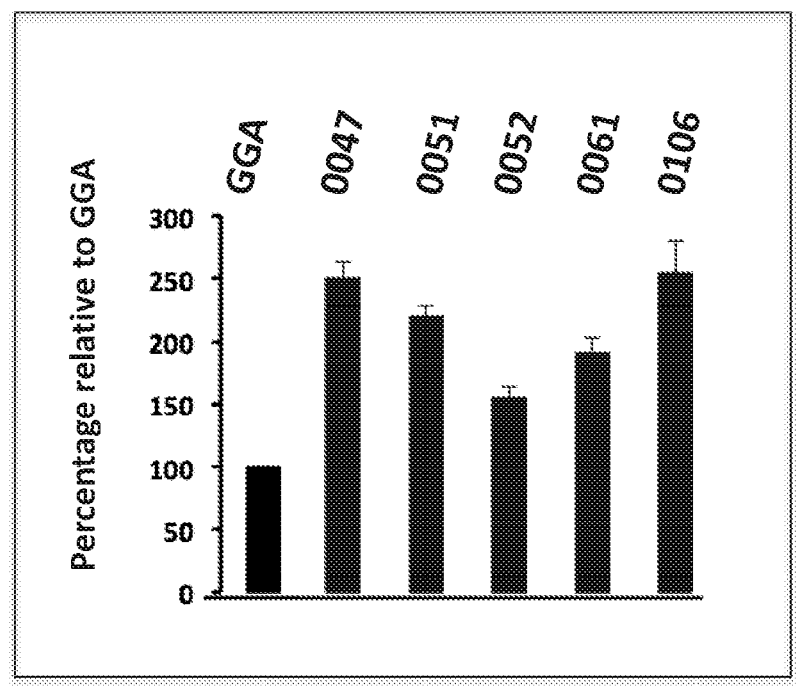

FIG. 1: Exemplary compounds according to Formula I wherein X is $X_1$.
FIG. 2: Exemplary compounds according to Formula I wherein X is $X_2$.
FIG. 3: Exemplary compound according to Formula I wherein X is $X_3$.
FIG. 4: Exemplary compounds according to Formula I wherein X is $X_4$.
FIG. 5: Exemplary compounds according to Formula I wherein X is $X_5$.
FIG. 6: Exemplary compounds according to Formula I wherein X is $X_6$.
FIG. 7: Exemplary compounds according to Formula II.
FIG. 8: Hsp70 induction in renal tubular cells by various GGA-like compounds. GGA was used as positive control. For details see Example 3. Panel A: Exemplary Western blot analysis. Panel B: densitometric analysis of the signal intensity for Hsp70 normalized to actin.

EXAMPLES

Example 1: Synthesis of Exemplary Analogs

Synthetic Route for Compound 76 (Taken as an Example)

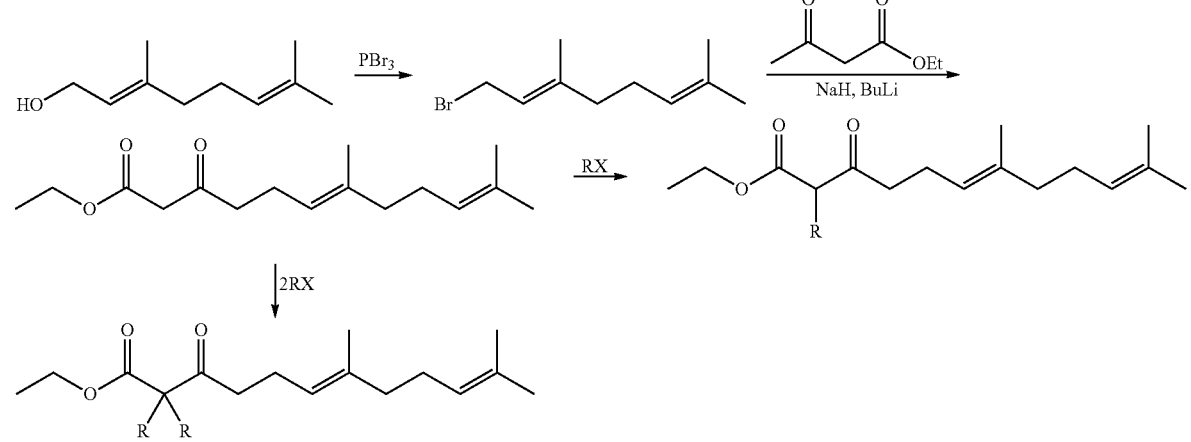

Synthesis of
(E)-1-bromo-3,7-dimethylocta-2,6-diene

Geraniol (10 g, 11.4 mL, 64.8 mmol, 1.0 eq) was dissolved in DCM (50 mL) under a nitrogen atmosphere. The solution was cooled to −20° C. A solution of $PBr_3$ (3.0 mL, 32.4 mmol, 0.5 eq) in DCM (10 mL) was added drop-wise, keeping the temperature <−16° C. The color changed to green/blue during addition. The reaction mixture was stirred for 3 h at ∼−20° C. Water (50 mL) was added carefully at −40° C. The water layer was extracted with $Et_2O$ (3×50 mL). The combined organic layers were washed with sat. aq. $NH_4Cl$. sol. (3×50 mL), dried over $Na_2SO_4$ and concentrated in vacuo to provide a brown oil (14.5 g, 66.6 mmol, quant.)

Synthesis of (E)-Ethyl 7,11-dimethyl-3-oxododeca-6,10-dienoate (Compound 21)

NaH (60% in oil, 2.63 g, 65.8 mmol, 1.0 eq) was suspended in THF (20 mL), under a nitrogen atmosphere. The solution was cooled to 0° C. with an ice/water bath. Ethylacetoacetate (8.3 mL, 65.8 mmol, 1.0 eq) was added drop-wise in 1 h. During addition a thick suspension was formed which later became a yellow solution. Gas formation was visible and an exothermic reaction was observed. The temperature was kept <10° C. The reaction mixture was stirred for 10 min at 0° C. n-BuLi (2.5M in hexanes, 26.3 mL, 65.8 mmol, 1.0 eq) was added drop-wise in 10 min. An exothermic reaction was observed. During addition the flask was cooled with an ice/MeOH bath. A bright yellow suspension was formed which changed into a yellow solution. The temperature was kept at 0° C. for 10 min. Geranylbromide (9.1 mL, 46.1 mmol, 0.7 eq) was added drop-wise and a suspension was formed. The reaction mixture was warmed to room temperature and stirred for 1 h. The reaction mixture was poured in sat. aq. NH$_4$Cl sol. (100 mL) and the water layer was extracted with TBME (3×100 mL). The combined organic layers were dried over Na$_2$SO$_4$ and concentrated in vacuo to provide a yellow oil (17.1 g). The crude product was purified by automated column chromatography (eluents, 0 to 100% DCM in heptanes) affording a colorless oil (6.0 g, 22.4 mmol, 49%).

$^1$H-NMR (CDCl$_3$, in ppm)): δ 1.30 (t, 3H), 1.60 (s, 6H), 1.69 (s, 3H), 2.02 (m, 4H), 2.31 (m, 2H), 2.60 (t, 2H), 3.44 (s, 2H), 4.10 (q, 2H), 5.06 (t, 2H). M+=267.

Synthesis of (E)-ethyl 2,2,7,11-tetramethyl-3-oxododeca-6,10-dienoate (Compound 76)

NaH (70 mg, 1.8 mmol, 2.6 eq) was suspended in TFH (6 mL), under a nitrogen atmosphere, and cooled to 0° C. with an ice/water bath. A solution of compound 21 (180 mg, 0.68 mmol, 1.0 eq) in THF (20 mL) was added and allowed to warm to room temperature and subsequently stirred for 30 min. A solution of MeI (101 μL, 1.6 mmol, 2.4 eq) in THF (20 mL) was added and the reaction mixture was heated to reflux temperature and stirred overnight. The solvents were removed in vacuo. Water (30 mL) was added and the water layer was extracted with TBME (3×30 mL) and EtOAc (1×30 mL). The combined organic layers were dried over Na$_2$SO$_4$ and concentrated in vacuo. The crude product was purified by automated column chromatography (eluens 0 to 100% DCM in heptanes) affording a colorless oil (20.1 mg, 0.068 mmol, 10%)

$^1$H-NMR (CDCl$_3$, in ppm)): δ 1.25 (t, 3H), 1.35 (s, 6H), 1.60 (s, 6H), 1.67 (s, 3H), 2.01 (m, 4H), 2.25 (m, 2H), 2.49 (t, 2H), 4.20 (q, 2H), 5.04 (t, 2H). M+=295.

Synthetic Route for Compound 28 (Taken as an Example)

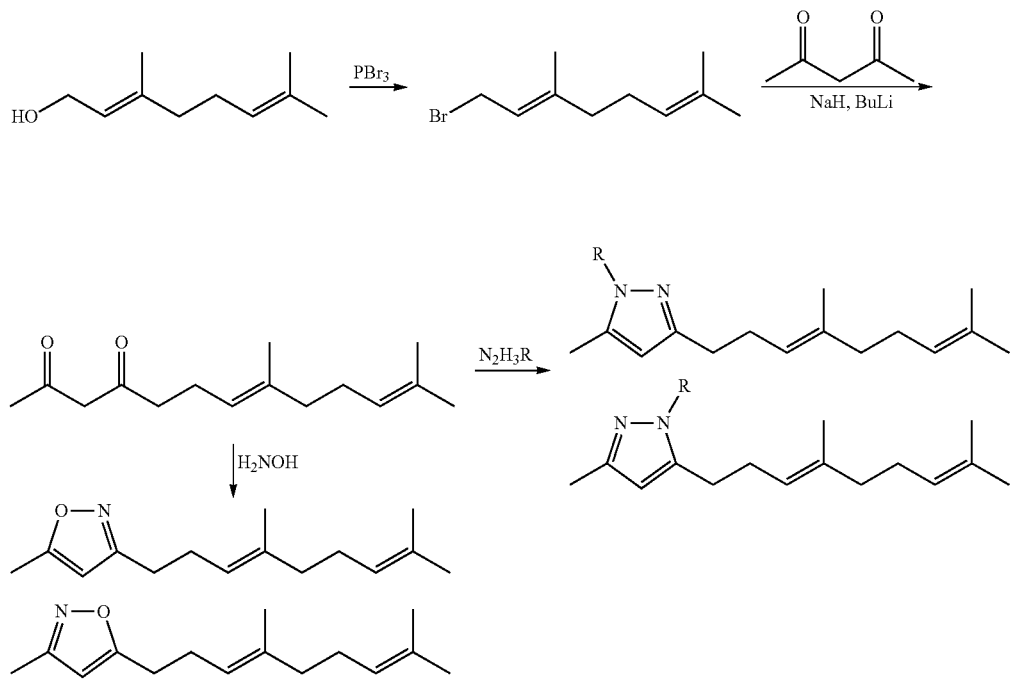

Synthesis of (E)-8,12-Dimethyltrideca-7,11-Diene-2,4-Dione (Compound 28)

Sodium hydride (60%, 2 g, ca. 50 mmol) was added under nitrogen atmosphere to THF (125 mL) while stirring. The suspension was cooled to 0° C. for 10 minutes and 2,4-pentanedione (5 g, 50 mmol) was added drop-wise over ca. 3 minutes. A slightly exothermic reaction took place, resulting in some gas evolution and a thick white suspension was obtained. nBuLi (19 mL, 2.5 M in hexanes) was added in ca. 15 seconds with a plastic syringe. A slightly yellow, clear solution was obtained. After 20 minutes geranyl bromide (7.3 g, 33.62 mmol) was added. The resulting suspension was stirred while warming to room temperature for 1 hour. The reaction mixture was quenched with sat. aq. NH$_4$Cl (70 mL). Extraction with TBME (2×150 mL), drying of the organic fractions with Na$_2$SO$_4$ and concentration under vacuum gave the crude product (9.66 g, >100%). Purification of a small sample by ISCO chromatography afforded (E)-8,12-dimethyltrideca-7,11-diene-2,4-dione (63 mg) as an oil.

$^1$H-NMR (CDCl$_3$, in ppm)): δ 1.60 (s, 6H), 1.69 (s, 3H), 2.01 (m, 4H), 2.10 (s, 3H), 2.30 (m, 4H), 3.60 (s, 2H), 5.08 (t, 2H). M+=237.

Synthetic Route for Compound 62 (Taken as an Example)

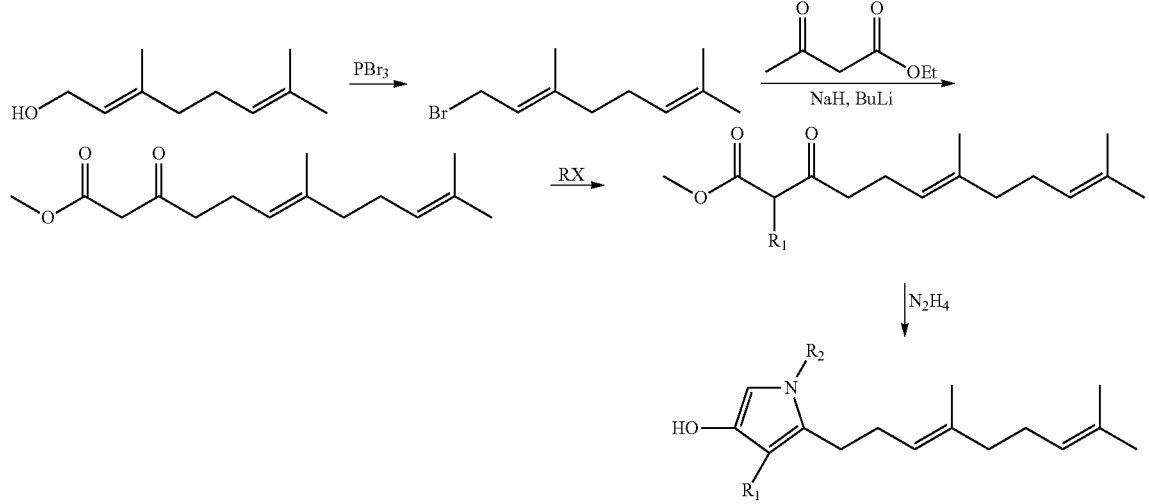

Synthesis of (E)-5-(4,8-dimethylnona-3,7-dien-1-yl)-1H-pyrazol-3-ol (Compound 62)

Compound 21 (500 mg, 1.88 mmol, 1.0 eq) was dissolved in EtOH (10 mL), under a nitrogen atmosphere. The solution was cooled to 0° C. with an ice/water bath. Hydrazine (64% water, 0.12 mL, 2.44 mmol, 1.3 eq) was added and the solution was warmed to room temperature overnight. The solvents were removed in vacuo and Et$_2$O (10 mL) was added to the residue. The solids were isolated by filtration and purified by automated column chromatography (eluens, 50 to 100% EtOAc in heptanes) yielding a white solid (81 mg, 0.35 mmol, 18%).

$^1$H-NMR (CDCl$_3$, in ppm)): δ 1.61 (s, 6H), 1.65 (s, 3H), 2.05 (m, 4H), 2.30-2.65 (m, 4H), 3.60 (s, 2H), 5.06 (m, 2H), 5.48 (s, 1H). M+=235.

Synthetic Route for Compound 51 and 52 (Compound 51 is Taken as an Example).

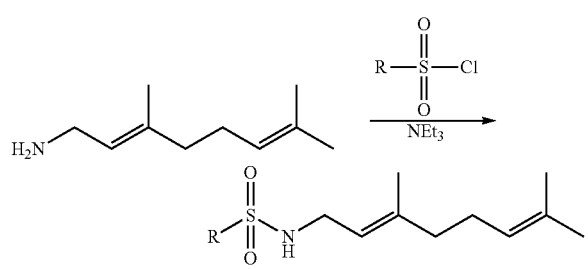

Synthesis of (E)-N-(3,7-Dimethylocta-2,6-dien-1-yl) methanesulfonamide (Compound 51)

A solution of geranylamine (306 mg, 2.0 mmol) and triethylamine (360 mg, 3.6 mmol) in dichloromethane (2 mL) was cooled to 0° C. with an ice bath and methanesulphonyl chloride (229 mg, 2 mmol) was added. After stirring overnight while warming to room temperature water (10 mL) was added. Extraction with dichloromethane (2×10 mL), drying of the combined organic layers with Na$_2$SO$_4$ and concentration under vacuum provided crude compound 51. Purification by ISCO chromatography afforded (E)-N-(3,7-dimethylocta-2,6-dien-1-yl)methanesulfonamide (208 mg, 0.90 mmol, 45%).

$^1$H-NMR (CDCl$_3$, in ppm)): δ 1.60 (s, 3H), 1.66 (s, 6H), 2.08 (m, 4H), 2.97 (s, 3H), 3.79 (t, 2H), 5.04 (t, 1H), 5.21 (t, 1H). M+=232.

Synthetic Route for Compound 61 (Taken as an Example)

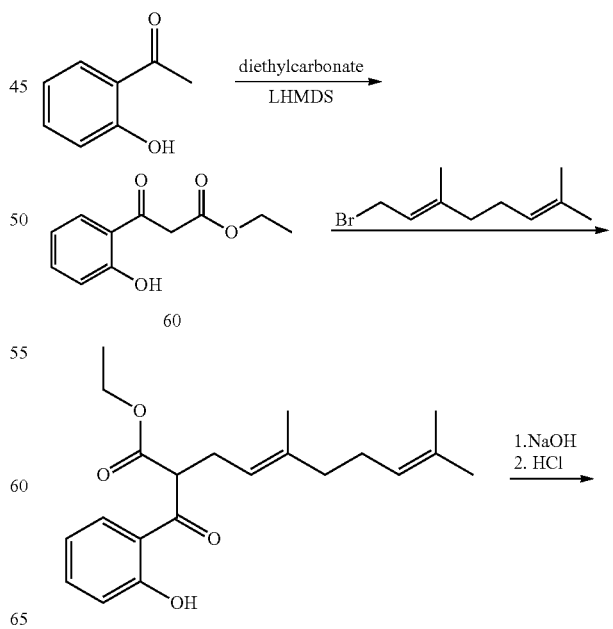

-continued

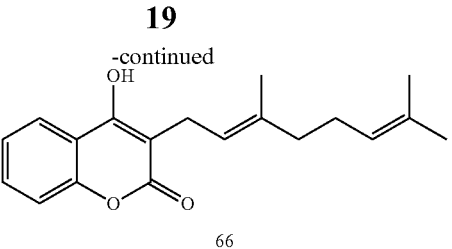

66

Synthesis of Ethyl 3-(2-hydroxyphenyl)-3-oxopropanoate (Compound 60)

A solution of LHMDS (1M, 220 mL, 220 mmol, 3.0 eq) was under $N_2$ atmosphere cooled to −78° C. A solution of 2'-hydroxyacetophenone (8.84 mL, 73.5 mmol, 1.0 eq) in THF (300 mL) was added drop-wise in 30 min. The temperature was maintained at −78° C. for 1 h and 2 h at −10° C. The solution was cooled again to −78° C. and subsequently a solution of diethylcarbonate (9.8 mL, 80.8 mmol 1.1 eq) in THF (30 mL) was added. The reaction mixture was allowed to warm to room temperature over the weekend and poured in a mixture of HCl (37%, 50 mL) and ice (1.5 L). The layers were separated and the water layer was extracted with DCM (2×500 mL). The combined organic layers were washed with brine (1×0.5 L), dried over $Na_2SO_4$ and concentrated in vacuo yielding a yellow oil (16.4 g). The crude product was stirred in DCM and the solids formed were removed by filtration. The filtrate was purified by automated column chromatography (eluens, 0 to 30% EtOAc in heptanes) affording a colorless oil (11.6 g, 55.6 mmol, 76%).

$^1$H-NMR (CDCl$_3$, in ppm)): δ 1.27 (t, 3H), 4.01 (s, 2H), 4.23 (q, 2H), 6.97 (t, 1H), 7.00 (d, 1H), 7.55 (t, 1H), 7.64 (d, 1H). M+=209.

Synthesis of (E)-Ethyl 2-(2-hydroxybenzoyl)-5,9-dimethyldeca-4,8-dienoate (Compound 61)

Diisopropylamine (3.6 mL, 41.4 mmol, 4.5 eq) was dissolved in THF (25 mL), under a nitrogen atmosphere. The solution was cooled to −20° C. n-BuLi (2.5M, 14.7 mL, 36.8 mmol, 4.0 eq) was added subsequently. After stirring for 5 min at −20° C. the reaction mixture was cooled to −78° C. A solution of compound 60 (3.8 g, 18.4 mmol, 2.0 eq) in THF (20 mL) was added. The reaction mixture was stirred for 1 h at <−70° C. and 2 h at <−10° C. and cooled again to −78° C. A solution of geranylbromide in THF (10 mL) was added. The reaction mixture was allowed to warm to room temperature overnight and poured in a mixture of brine (100 mL) and sat. aq. $NH_4Cl$ sol. (100 mL). The water layer was extracted with DCM (1×100 mL and 2×50 mL). The combined organic layers were dried over $Na_2SO_4$ and concentrated in vacuo yielding a brown oil (5.9 g). The crude product was purified by automated column chromatography (eluens 0 to 30% EtOAc in heptanes) furnishing a yellow oil (0.69 g, 2.0 mmol, 22%).

$^1$H-NMR (CDCl$_3$, in ppm)): δ 1.21 (t, 3H), 1.57 (s, 3H), 1.62 (s, 6H), 2.00 (m, 4H), 2.78 (m, 2H), 4.18 (q, 2H), 4.38 (t, 1H), 5.07 (m, 2H), 6.98 (t, 1H), 7.02 (d, 1H), 7.55 (t, 1H), 7.81 (d, 1H). M+=345.

Example 2: Biological Activity of Novel Analogs

This Example demonstrates the biological activity of various representative compounds of the invention. Compounds were screened for their ability to 1) boost HSP protein and mRNA expression in a mammalian cell-line, 2) induce programmed cell death in a human cancer cell-line, 3) protect against loss of contractile function induced by tachypacing.

Materials and Methods
Cell Culture and Heat Shock Conditions:
HL-1 Cardiomyocytes HL-1 atrial myocytes, a cell line derived from adult mouse atria were obtained from Dr. William Claycomb (Louisiana State University, New Orleans, La., USA). The myocytes were maintained in Complete Claycomb Medium (JRH, UK) supplemented with 100 μM norepinephrine stock (consisting of 10 mM norepinephrine (Sigma, The Netherlands) dissolved in 0.3 mM L-ascorbic acid (Sigma)), 4 mM L-glutamine (Gibco, The Netherlands) and 10% FBS (Sigma). The myocytes were cultured in flasks coated with 0.02% gelatin (Sigma), in a 5% $CO_2$ atmosphere at 37° C.

HL-1 cardiomyocytes were subjected to a mild heat shock of 44° C. for 10 minutes. After a recovery of 10 minutes (37 degrees 5% $CO_2$), compounds were added in a final concentration of 10 μM (dissolved in DMSO, final concentration 0.1%). To control myocytes, 0.1% DMSO was added. After six hours the cells were lysed in RIPA buffer and used for Western blotting as described previously.[3, 10]

HL-1 Cardiomyocyte Tachypacing

HL-1 cardiomyocytes were cultured on coverslips and showed spontaneous contraction at ~1 Hz. The cardiomyocytes were tachypaced with a C-Pace100™-culture pacer in C-Dish100™-culture dishes (IonOptix Corporation, The Netherlands), at 4 Hz with square-wave 20-msec pulses (40 V). Capture was ascertained by microscopic examination of cell shortening. We required a capture efficiency of >90% of cardiomyocytes throughout stimulation. HL-1 cardiomyocytes were pretreated with test compound (10 μM) for 8 hours, followed by tachypacing at 4.5 Hz or normal pacing at 1 Hz. After pacing, HL-1 cardiomyocytes were used to measure the calcium transient (CaT) as a read out for contractile function.

Live Imaging and Measurement of CaT

To measure CaT, 2 μM of the $Ca^{2+}$-sensitive Fluo-4-AM dye (Invitrogen, The Netherlands) was loaded into HL-1 cardiomyocytes by 45 min incubation, followed by 3 times washing with DMEM solution. $Ca^{2+}$ loaded myocytes were excited by 488 nm and light emitted at 500-550 nm and visually recorded with a 40×-objective, using a Solamere-Nipkow-Confocal-Live-Cell-Imaging system (based on a Leica DM IRE2 Inverted microscope). The live recording of CaT in HL-1 cardiomyocytes was performed at 1 Hz of stimulation in a temperature (37° C.) controlled system. By use of the software ImageJ (National Institutes of Health, USA), the absolute value of fluorescent signals in live cardiomyocytes were recorded and analyzed. To compare the fluorescent signals between experiments, the following calibration was utilized: $F_{cal}=F/F0$, in which (F) is fluorescent dye at any given time and (F0) is fluorescent signal at rest [10]. Mean values from each experimental condition were based on 7 consecutive CaT in at least 50 myocytes.

MCF-7 Cells

MCF-7 breast cancer cells were cultured in DMEM supplemented with 10% FCS. Test compounds were added to the medium in a final concentration of 10 for 16-20 hours. Ratio death and living cells was determined by using trypan blue staining of death cells. The cell pellets were lysed in RIPA buffer and used for Western blot analysis.

Protein-Extraction and Western Blot Analysis

Western-blot analysis was performed as described previously[3, 10]. Equal amount of protein in SDS-PAGE sample buffer was sonicated before separation on 10% PAA-SDS gels. After transfer to nitrocellulose membranes (Stratagene, The Netherlands), membranes were incubated with primary antibodies against HSP25 (Stressgen, The Netherlands, SPA-801, 1:1000), HSP27 (Stressgen, SPA-800, 1:1000), HSP70 (Stressgen, SPA-810, 1:1000), GAPDH (Affinity Reagents, The Netherlands) or PARP (Santa Cruz, The Netherlands, sc-7150, 1:500). Horseradish peroxidase-conjugated anti-mouse or anti-rabbit (Santa-Cruz Biotechnology, The Netherlands) was used as secondary antibody. Signals were detected by the ECL-detection method (Amersham, The Netherlands) and quantified by densitometry using GeneTools software from Syngene (The Netherlands).

Statistical Analysis

Results are expressed as mean±SEM. All experimental procedures were performed in at least duplicate series. ANOVA was used for multiple-group comparisons. Student t tests were used for comparisons involving only 2 groups, and 1 tests with Bonferroni correction were used to compare individual group differences when multiple-comparison ANOVA was significant. All P values were two-sided. $P<0.05$ was considered statistically significant. SPSS version 16.0 was used for statistical evaluation.

Results

Screening for Analogs Capable of Boosting HSP70 Levels in HL-1 Cardiomyocytes.

Compounds were also screened for HSP70 boosting effects. Hereto, HL-1 cardiomyocytes were first subjected to a mild heat shock which activates the Heat Shock Factor. After the mild heat shock, compound (10 μM) was added to the medium of HL-1 cardiomyocytes for 6 hours, followed by determination of the HSP70 amount. We observed that exemplary analogs 23, 28, 46, 49, 51, 52, 60 61, 62, 76 and 95 are potent inducers of mammalian HSP70 protein expression (Table 1).

TABLE 1

Biological activity of GGA-analogs.

| | HSP boosting HL-1 cardiomyocytes | | | | | | Cell Death | | | | Contractile function |
|---|---|---|---|---|---|---|---|---|---|---|---|
| | | mRNA (qPCR) | | | | | | MCF-7 cancer cells | | | HL-1 |
| | | | | | | Grp78 | | | | | |
| Compound | Protein HSP70 | HSP 70 | HSP 25 | HSP 90 | HSP 40 | Not HSF1 | Death/living 100 μM | HSP 27 | HSP 70 | PARP | Protection CaT |
| No drug | 0 | 1 | 1 | 1 | 1 | 1 | 4.5 | 1 | 1 | 1 | −50% |
| GGA | ++ | + | ++ | ++ | + | 0 | 0 | + | 0 | 0 | ++++ |
| FA | 0 | | | | | | ND | | | | |
| GA | ++ | | | | | | ND | | | | |
| 21 | 0 | | | | | | | | | | |
| 22 | 0 | | | | | | | | | | |
| 23 | ++++ | ++ | + | + | + | 0 | | | | | − |
| 24 | 0 | | | | | | | | | | |
| 26 | 0 | | | | | | 0 | 0 | 0 | + | |
| 28 | ++++ | + | + | + | + | 0 | 0 | ++ | 0 | 0 | ++++ |
| 32 | + | | | | | | 0 | + | 0 | 0 | |
| 33 | + | | | | | | | | | | |
| 34 | 0 | | | | | | | | | | |
| 35 | 0 | | | | | | | | | | |
| 36 | 0 | | | | | | 0 | − | − | 0 | |
| 39 | 0 | | | | | | 0 | + | 0 | 0 | |
| 40 | 0 | | | | | | | | | | |
| 41 | 0 | | | | | | + | + | 0 | + | |
| 43 | 0 | | | | | | | | | | |
| 44 | 0 | | | | | | | | | | |
| 45 | 0 | | | | | | ++ | 0 | − | ++ | |
| 46 | ++ | + | ++ | ++ | + | 0 | | | | | − |
| 49 | +++ | ++++ | +++ | +++ | +++ | 0 | 0 | 0 | 0 | 0 | − |
| 51 | ++++ | + | + | + | + | 0 | 0 | ++ | + | 0 | ++++ |
| 52 | ++++ | + | + | + | + | 0 | | | | | ++++ |
| 53 | + | | | | | | | | | | |
| 56 | 0 | | | | | | 0 | 0 | 0 | 0 | |
| 61 | ++ | + | + | + | + | 0 | 0 | 0 | 0 | 0 | ++++ |
| 62 | ++ | + | 0 | + | + | 0 | | | | | ++++ |
| 64 | 0 | | | | | | | | | | |
| 65 | 0 | | | | | | ++ | +++ | ++ | ++ | |
| 66 | 0 | | | | | | 0 | + | ++ | + | |
| 67 | 0 | | | | | | 0 | 0 | 0 | 0 | |
| 68 | 0 | | | | | | 0 | +++ | ++ | + | |
| 69 | 0 | | | | | | | | | | |
| 70 | 0 | | | | | | 0 | +++ | ++ | 0 | |
| 76 | +++ | +++ | ++ | ++ | + | 0 | ND | | | | ++++ |
| 78 | 0 | | | | | | 0 | ++ | 0 | + | |
| 79 | + | | | | | | ND | | | | |
| 81 | 0 | | | | | | | | | | |
| 82 | 0 | | | | | | ND | | | | |
| 84 | + | | | | | | | | | | |
| 85 | 0 | | | | | | 0 | − | − | + | |

TABLE 1-continued

Biological activity of GGA-analogs.

| | | HSP boosting HL-1 cardiomyocytes | | | | | Cell Death | | | | Contractile function |
| | | mRNA (qPCR) | | | | | | | | | HL-1 |
| | | | | | | Grp78 | MCF-7 cancer cells | | | | |
| Compound | Protein HSP70 | HSP 70 | HSP 25 | HSP 90 | HSP 40 | Not HSF1 | Death/living 100 µM | HSP 27 | HSP 70 | PARP | Protection CaT |
|---|---|---|---|---|---|---|---|---|---|---|---|
| 89 | + | | | | | | 0 | 0 | 0 | 0 | |
| 91 | + | | | | | | | | | | |
| 95 | +++ | ++++ | + | ++ | + | 0 | | | | | − |
| 97 | 0 | | | | | | | | | | |
| 98 | 0 | | | | | | 0 | ++ | 0 | 0 | |
| 99 | 0 | | | | | | 0 | − | 0 | 0 | |
| 100 | 0 | | | | | | 0 | + | − | 0 | |
| 101 | 0 | | | | | | ++ | 0 | − | ++ | |
| 103 | 0 | | | | | | 0 | 0 | 0 | 0 | |
| 104 | = | | | | | | | | | | |
| 124 | + | | | | | | | | | | |
| 125 | 0 | | | | | | | | | | |
| 127 | 0 | | | | | | 0 | − | 0 | 0 | |
| 128 | 0 | | | | | | | | | | |

Induction of MCF-7 Cell Death: 0 = no dead cells;
+ = $P < 0.05$;
++ = $P < 0.01$;
+++ = $P < 0.001$;
ND = not determined.
HSP boosting effect in HL-1; 0 = no induction HSP levels;
+ = 2-10-fold induction;
++ = 10-30-fold induction;
+++ = > 30-fold induction Upregulation of Mammalian HSP mRNA Levels Compounds were also screened for their ability to upregulate HSP gene expression. Hereto, HL-1 cardiomyocytes were first subjected to a mild heat shock which activates the Heat Shock Factor. After the mild heat shock, compound (10 µM) was added to the medium of HL-1 cardiomyocytes for 6 hours, followed by determination of HSP70, HSP25, HSP90 and HSP40 which are targets of the heat shock factor 1 (HSF1) transcription factor. In addition, we determined mRNA levels of the gene encoding the glucose-responsive protein 78 (Grp78) which is HSF1-independent. We observed that exemplary GGA analogs 23, 28, 46, 51, 52, 60, 61, 62 and 76 are strong inducers of HSP gene expression, while no upregulation of Grp78 mRNA was observed (Table 1). This indicates that regulation of HSP gene expression by a compound of the invention is mediated via HSF-1.

Screening for Compounds Able to Induce Programmed Cell Death.

Since we observed that some compounds aggravate tachypacing-induced contractile dysfunction, we next investigated if these compounds can induce programmed cell death in a human breast cancer cell-line MCF-7. Hereto, MCF-7 cells were incubated for 16 hours with 10 µM of a test compound after which the number of death and living cells was determined. In total 28 compounds were tested for cell death. Four compounds (41, 45, 65 and 101) showed a significant increase in cell death, which correlated with an aggravation of contractile dysfunction. GGA was used as a control as well as non-treated MCF-7 cells. Compounds 26, 41, 45, 65, 66, 68, 78, 85, and 101 induced PARP cleavage, indicative of pro-apoptotic caspase activation. The findings indicate that GGA-like compounds which aggravate heart failure can induce programmed cell death in MCF-7 breast cancer cell-line.

Example 3

Effect of GGA-Like Compounds on Renal Cells

This example illustrates that GGA-like compounds also find their use in the prevention or therapy of renal injury.

It has been shown by Wang et al. (Kidney International (2011) 79, 861-870) that the kidney cortical Hsp70 content inversely correlates with tubular injury, apoptosis, and organ dysfunction after injury. It was also found that increased Hsp70 expression mice reduces both ischemic tubular injury and organ dysfunction. When administered after ischemia, this inducer also decreased tubular injury and organ failure. Thus, increasing Hsp70 either before or after ischemic injury preserves renal function by attenuating acute kidney injury.

The present inventors therefore evaluated the effect of various GGA-like compounds on the induction of Hsp70 expression in murine proximal tubule cells.

Murine proximal tubule (MPT) cells were isolated and cultured as described previously (Borkan et al. Heat stress ameliorates ATP depletion-induced sublethal injury in mouse proximal tubule cells. Am. J. Physiol. 1997; F347-55).

The MPT cells were exposed to 40 µM of compound for 5 hours, after which the cells were harvested in RIPA buffer followed by Western blotting.

For Western-blot analysis, equal amount of protein in SDS-PAGE sample buffer was separated on 10% PAA-SDS gels. After transfer to nitrocellulose membranes (Stratagene, USA), membranes were incubated with primary antibodies against HSP70 (Enzo C92F3A/StressGen SP810) or beta-actin (Sigma A541). Horseradish peroxidase-conjugated anti-mouse or anti-sheep (Jackson ImmunoRes) was used as secondary antibody. Signals were detected by the ECL-detection method (Amersham).

It was found that compounds 32, 46, 47, 49, 51, 52, 61, 62, 69, 95 and 106 were strong inducers of HSP70 expression in renal cells, and even outperformed the inducing capacity of the positive control GGA. FIG. 8 shows exemplary Western blot analysis and densitometric quantification of HSp70 induction.

These data indicate that the compounds find their use in the prevention of injury to renal tubular cells, for example attenuating acute kidney injury (AKI), by increasing Hsp70 either before or after ischemic injury.

REFERENCES (1) Hirakawa T et al. *Gastroenterology* 1996; 111:345-57.
(2) Shirakabe H et al. *Clinical Therapeutics* 1995; 17:924-35.
(3) Brundel B J J M et al *Circ Res* 2006; 99:1394-402.
(4) Sakabe M et al. *Cardiovasc Res* 2008; 78:63-70.
(5) Zhang D et al. *J Mol Cell Cardiol* 2011; 51:381-9.
(6) Brundel B J J M et al. *Cardiovasc Res* 2008; 78:422-8.
(7) Sanbe A et al. *PlosOne* 2009; 4:e5351.
(8) Katsuno M et. al. *Proc Natl Acad Sci USA* 2005; 102:16801-6.
(9) Yoshikawa N et al. *Anticancer Drugs* 2010; 21:850-60.
(10) Brundel B J J M et al. *J Mol Cell Cardiol* 2006; 41:555-62.

The invention claimed is:

1. A pharmaceutical composition comprising a compound of the general formula I

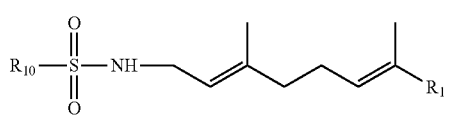

(I)

wherein
R$_1$ is H or a saturated or unsaturated aliphatic moiety comprising 1 to 8 C-atoms; and
wherein R$_{10}$ is a C$_1$-C$_5$ alkyl group, optionally substituted with one or more selected from the group consisting of halogen, oxo, sulfo, hydroxyl, —CN, alkoxy, amino, amido, aryl, substituted aryl, hetero-aryl, substituted hetero-aryl, cyclo-alkyl, heterocycloalkyl, nitro, carboxylic acid and carboxylic ester;
or a pharmaceutically acceptable salt thereof and a pharmaceutically acceptable carrier and/or adjuvant.

2. A method of treatment of a disease which is associated with loss of proteostatic control, including the accumulation of misfolded proteins and/or the presence of damaged proteins, comprising administering to a subject in need thereof a pharmaceutical composition according to claim 1.

3. A method of treatment of a disease which is associated with ischemia/reperfusion injury, comprising administering to a subject in need thereof a pharmaceutical composition according to claim 1.

4. A method for the treatment of a disease which is associated with loss of proteostatic control, including the accumulation of misfolded proteins and/or the presence of damaged proteins or a disease which is associated with ischemia/reperfusion injury, comprising administering to a subject in need thereof a pharmaceutical composition according to claim 1.

5. The pharmaceutical composition of claim 1, wherein R$_{10}$ is a C$_1$-C$_5$ alkyl group, optionally substituted with one, two, or three halogens.

6. The pharmaceutical composition of claim 1, wherein the compound of general formula (I) is compound 51 or compound 52:

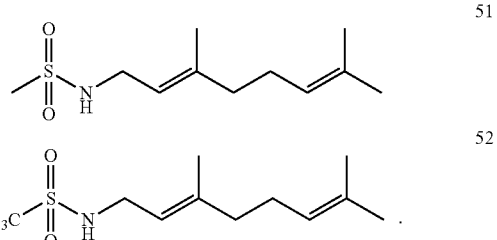

7. The method of claim 4, wherein the disease is supraventricular arrhythmia.

8. The method of claim 4, wherein the pharmaceutical composition comprises compound 51 or compound 52:

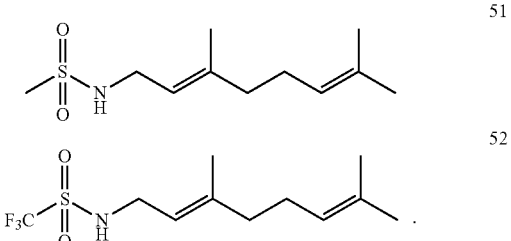

* * * * *